(12) United States Patent
Schnarr et al.

(10) Patent No.: US 11,679,281 B1
(45) Date of Patent: Jun. 20, 2023

(54) SCALABLE SLIM RADIOTHERAPY TREATMENT DELIVERY SYSTEM TOPOLOGY

(71) Applicant: Accuray Incorporated, Sunnyvale, CA (US)

(72) Inventors: Eric Schnarr, McFarland, WI (US); Mark Trail, Sunnyvale, CA (US); Calvin Maurer, Jr., San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 17/830,107

(22) Filed: Jun. 1, 2022

(51) Int. Cl.
*A61N 5/10* (2006.01)
*G21K 5/04* (2006.01)

(52) U.S. Cl.
CPC ............ *A61N 5/1081* (2013.01); *A61N 5/10* (2013.01); *A61N 5/103* (2013.01); *A61N 5/1039* (2013.01); *A61N 5/1048* (2013.01); *A61N 5/1049* (2013.01); *A61N 5/1077* (2013.01); *A61N 5/1078* (2013.01); *A61N 5/1082* (2013.01); *G21K 5/04* (2013.01); *A61N 2005/1052* (2013.01); *A61N 2005/1054* (2013.01); *A61N 2005/1055* (2013.01); *A61N 2005/1061* (2013.01)

(58) Field of Classification Search
CPC ........ A61N 5/10; A61N 5/103; A61N 5/1031; A61N 5/1037; A61N 5/1039; A61N 5/1048; A61N 5/1049; A61N 2005/1052; A61N 2005/1054; A61N 2005/1055; A61N 2005/1061; A61N 5/1064; A61N 5/1065; A61N 5/1067; A61N 5/1069; A61N 5/107; A61N 5/1077; A61N 5/1081; A61N 5/1082; A61N 5/1078
USPC ......................................................... 378/65
See application file for complete search history.

(56) References Cited

U.S. PATENT DOCUMENTS

| | | | | |
|---|---|---|---|---|
| 5,818,902 | A * | 10/1998 | Yu ...................... | A61N 5/1047 378/65 |
| 7,085,347 | B2 * | 8/2006 | Mihara ................ | A61N 5/1082 378/65 |
| 7,295,648 | B2 * | 11/2007 | Brown ................. | A61N 5/1082 378/65 |
| 7,391,849 | B2 * | 6/2008 | Smith .................. | A61N 5/1048 378/101 |
| 7,619,374 | B2 * | 11/2009 | Aoi ..................... | A61N 5/10 378/65 |
| 7,940,891 | B2 * | 5/2011 | Star-Lack ........... | A61B 6/0435 378/65 |
| 7,961,843 | B2 * | 6/2011 | Brown ................. | A61N 5/1047 378/65 |
| 8,126,114 | B2 * | 2/2012 | Naylor ................. | A61B 34/30 378/65 |

(Continued)

Primary Examiner — Allen C. Ho
(74) Attorney, Agent, or Firm — Womble Bond Dickinson (US) LLP

(57) ABSTRACT

A radiation delivery system that includes a gantry to extend along one or more axes. The gantry is to provide a continuous rotation. The radiation delivery system includes a linear accelerator (LINAC) coupled to the gantry. The LINAC is to generate a treatment beam. The radiation delivery system includes a rotary joint coupled to the gantry. The rotary joint provides a physical connection from the LINAC to an external system that is positioned off the gantry. The physical connection is to transport radio frequency (RF) power.

20 Claims, 6 Drawing Sheets

(56) References Cited

U.S. PATENT DOCUMENTS

| | | | | |
|---|---|---|---|---|
| 8,350,226 | B2 * | 1/2013 | Zdasiuk | H01J 37/1475 250/492.1 |
| 8,488,739 | B2 * | 7/2013 | Ziegler | A61N 5/1082 378/65 |
| 8,503,608 | B2 * | 8/2013 | Brown | A61N 5/1042 378/65 |
| 8,536,547 | B2 * | 9/2013 | Maurer, Jr. | A61B 6/4447 250/492.1 |
| 8,655,429 | B2 * | 2/2014 | Kuduvalli | B25J 9/1682 600/407 |
| 8,917,813 | B2 * | 12/2014 | Maurer, Jr. | A61B 6/06 378/65 |
| 8,983,573 | B2 * | 3/2015 | Carlone | A61N 5/1067 378/65 |
| 8,989,846 | B2 * | 3/2015 | Kuduvalli | A61B 6/4476 600/407 |
| 9,011,002 | B2 * | 4/2015 | Dirauf | A61N 5/1081 378/65 |
| 9,126,036 | B2 * | 9/2015 | Leek | A61N 5/1077 |
| 9,314,647 | B2 * | 4/2016 | Dirauf | A61B 6/4441 |
| 9,526,917 | B2 * | 12/2016 | Carlsson | A61N 5/1081 |
| 9,687,200 | B2 * | 6/2017 | Maurer, Jr. | A61B 6/032 |
| 9,731,148 | B2 * | 8/2017 | Olivera | A61B 5/055 |
| 10,315,049 | B2 * | 6/2019 | Gauthier | A61N 5/1039 |
| 10,342,996 | B2 * | 7/2019 | Jordan | A61N 5/1083 |
| 10,406,382 | B2 * | 9/2019 | Humber | A61B 6/4085 |
| 10,485,993 | B2 * | 11/2019 | Goer | A61N 5/1049 |
| 10,532,224 | B2 * | 1/2020 | Jordan | A61B 5/055 |
| 10,688,320 | B2 * | 6/2020 | Voronenko | A61N 5/1031 |
| 10,695,586 | B2 * | 6/2020 | Harper | A61N 5/1081 |
| 11,141,606 | B2 * | 10/2021 | Fallone | A61N 5/10 |
| 11,147,989 | B2 * | 10/2021 | Cox | A61N 5/1039 |
| 11,154,269 | B2 * | 10/2021 | Shea | A61B 6/5264 |
| 11,318,329 | B1 * | 5/2022 | Trail | H05H 7/02 |
| 11,524,181 | B2 * | 12/2022 | Ciresianu | A61N 5/1083 |

* cited by examiner

SCALABLE SLIM RADIOTHERAPY TREATMENT DELIVERY SYSTEM TOPOLOGY

TECHNICAL FIELD

The present disclosure relates to a radiation delivery system and, in particular, a radiation delivery system utilizing a rotary joint to allow subsystems to be located off a gantry.

BACKGROUND

In radiation treatment, a radiation delivery system may utilize a therapeutic radiation source to generate a treatment beam that provides a therapeutic dose of radiation to a target, such as a tumor of a patient. The radiation source may also operate in a mode that delivers a diagnostic imaging beam for the purposes of patient tumor imaging.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1A:
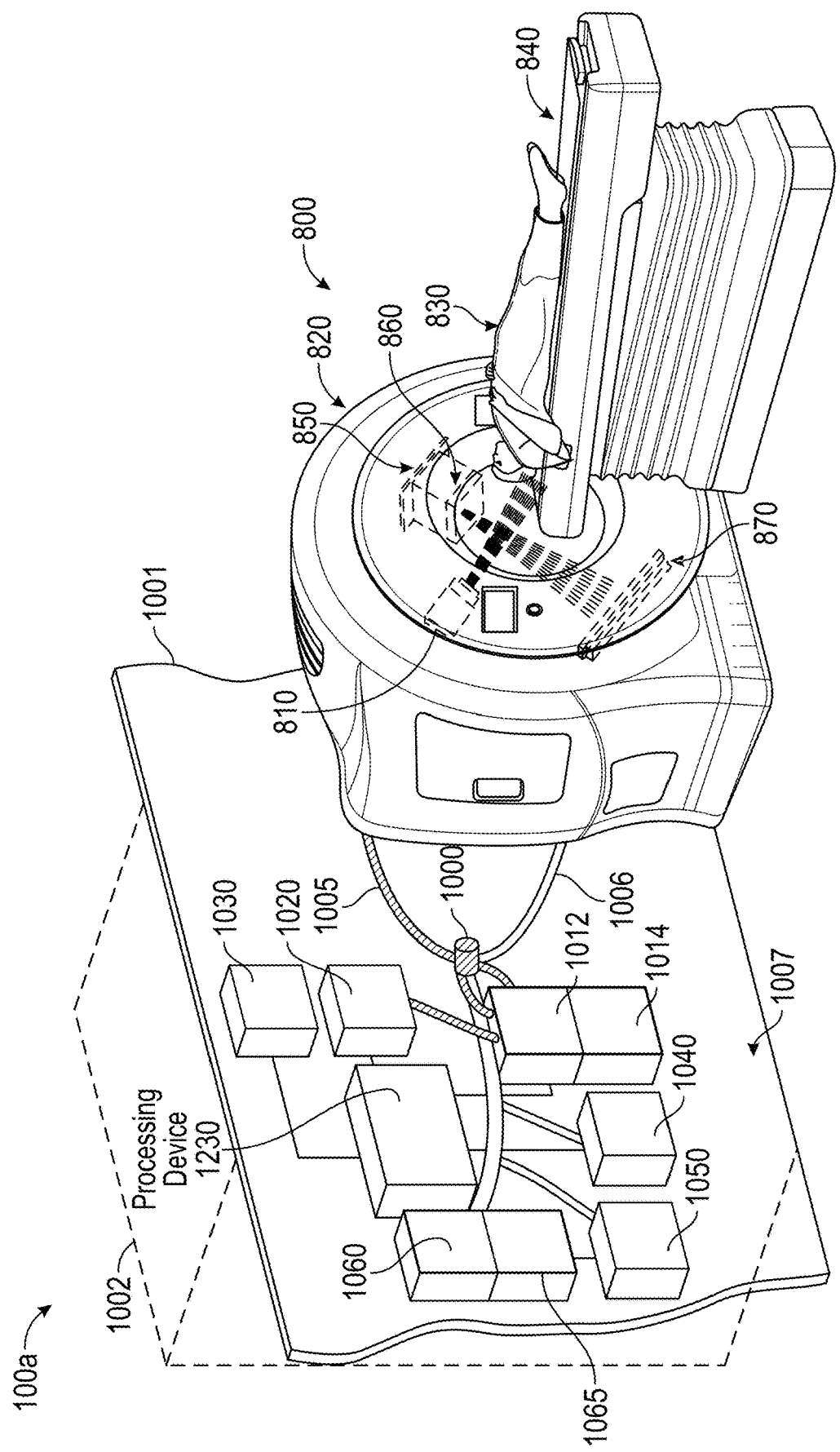
FIG. 1A illustrates a radiation delivery system, in accordance with embodiments described herein.

Described herein are embodiments for using a rotary joint to facilitate components of a radiation delivery system to be located off a gantry. The radiation delivery system may utilize a single radiation source that is capable of producing both imaging beams (also referred to as "diagnostic beams" hereafter) and treatment beams (also referred to as "therapeutic beams" hereafter) at different energy levels. The radiation source may be a magnetron, a klystron, or any other type of component capable of generating electromagnetic waves. The radiation source may be located off the gantry along with an energy adjuster to modulate the electromagnetic waves that are received from the radiation source used in the radiation delivery system. The energy adjuster may be a mechanical or electromechanical assembly that is configured to modulate an electromagnetic wave to correspond to an imaging beam, such as a kilovoltage (kV) imaging beam, or a treatment beam, such as a megavoltage (MV) treatment beam. Additional components of the radiation delivery system that may be located off the gantry comprise: a radio frequency isolator, a fluid temperature control unit, a power distribution unit, an air distribution unit, and a processing device as described in further detail herein. While located off the gantry, one or more of these components may make up an external system, which may be connected to a rotary joint. The rotary joint may bifurcate into a radio frequency (RF) waveguide for transmitting RF power to the gantry and a conduit (e.g., one or more channels) for transmitting electrical power, air, fluid, control, and high speed data signals to the gantry. The RF waveguide, while connected to the rotary joint, may be configured to match a continuous rotation of the gantry. The rotary joint may be coupled to a partition (sometimes referred to as, "physical barrier") to physically divide the external system from the gantry, and the rotary joint may comprise a slip ring as discussed in further detail herein.

In a conventional radiation delivery system, major radiation delivery subsystems (e.g., klystron, radio frequency isolator, fluid temperature control unit, etc.) are located on the stand, or gantry itself. To provide the major radiation delivery subsystems in such a manner, the radiation delivery system has tight packaging and a large outer volume. The large outer volume is the result in part of additional radio frequency interference (RFI), electromagnetic interference (EMI), and/or magnetic shielding that must be incorporated into the major radiation subsystems. Without the aforementioned shielding, the major radiation delivery subsystems would be unable to have their electronics function properly while located on the gantry itself because of their close proximity to electromagnetic radiation and/or a strong magnetic field. The radiation delivery system would be unable to operate properly, and treatment, imaging, and measurement capabilities/accuracy would be diminished as a result. Further, a conventional radiation delivery system may not have non-coplanar capabilities given how the conventional radiation delivery system is sized and configured based on having the major radiation delivery subsystems located on the gantry.

Aspects of the disclosure may remedy the above and other deficiencies by having a radiation delivery system implement a rotary joint that allows an external system comprising one or more of major radiation delivery subsystems to be positioned off a gantry. Locating the external system outside of a treatment room would remedy the need to provide EMI and/or magnetic shielding within the major radiation delivery subsystems, thereby reducing cost and size of components, so long as a barrier (e.g., a structural wall, a non-structural wall, a ceiling, a screen, etc.) provides the necessary shielding. Access to the external system for servicing purposes may also be easier by having one or more of major radiation delivery subsystems rack mounted compared to if the major radiation delivery subsystems were integrated directly on the gantry.

Additional benefits of moving the major radiation delivery subsystems off the gantry include a decluttered gantry (e.g., smaller size/footprint), which reduces patient-visible machine presence, thereby making the radiation delivery system less intimidating to patients. Further, the radiation delivery system may comprise a bore opening diameter up to 100 centimeters (cm), a short-axis distance (SAD) (which is the distance from the source of radiation to the axis of the gantry) up to 100 cm, a much shallower tunnel, and a way to provide non-coplanar capabilities as a result of the external system being located off the gantry. The radiation delivery system may reduce audible noise in the treatment room from having the external system located off the gantry and located outside of the treatment room. Audible noise in the treatment room may further be reduced by implementing magnetic direct drive capabilities in the radiation delivery system.

FIG. 1A illustrates a radiation delivery system 100a, in accordance with embodiments described herein. The radiation delivery system 100a may comprise a helical radiation delivery system 800, a rotary joint 1000, and an external system 1002.

The helical radiation delivery system 800 may include a linear accelerator (LINAC) 850 mounted to a rotatable gantry 820. The rotatable gantry 820 may rotate more than 360 degrees about the axis that extends from the head to the foot of a treatment couch 840. In doing so, the rotatable gantry 820 may provide a continuous rotation that may travel multiple rotations in excess of 360 degrees. The rotatable gantry 820 may be implemented or realized in any appropriate shape (e.g., ring, toroid, etc.) and/or using any appropriate material (e.g., metals, metallic alloys, polymers, etc.).

In some embodiments, the LINAC 850 may generate a radiation beam (i.e., treatment beam) by directing an electron beam towards an x-ray emitting target. The treatment beam may deliver radiation to a target region (i.e., a tumor). The helical radiation delivery system 800 further includes a multileaf collimator (MLC) 860 coupled with the distal end of the LINAC 850. The MLC 860 includes a housing that houses multiple leaves that are movable to adjust an aperture of the MLC 860 to enable shaping of the treatment beam. In some embodiments, the MLC 860 may be a binary MLC 860 that includes a plurality of leaves arranged in two opposing banks, where the leaves of the two opposing banks are interdigitated with one another and can be opened or closed to form an aperture. In some embodiments, the MLC 860 may be an electromagnetically-actuated MLC. In some embodiments, MLC 860 may be any other type of MLC.

In some embodiments, the rotatable gantry 820 may have a toroidal shape in which a patient 830 extends through a bore of the ring/toroid and the LINAC 850 is mounted on the perimeter of the ring and rotates about the axis passing through the center to irradiate a target region with beams delivered from one or more angles around the patient 830. During treatment of the patient 830, the helical radiation delivery system 800 may deliver a partial non-coplanar radiation beam by pivoting (e.g., tilting, rotating) the LINAC 850 (e.g., +/−fifteen degrees) out of the plane of rotation of rotatable gantry 820. A partial non-coplanar radiation beam of up to 30 degrees may be achieved when the LINAC 850 also comprises a gimbled head (not shown in FIG. 1A). Such functionality is able to be achieved by having the external system 1002 comprising one or more of major radiation delivery subsystems to be positioned off the rotatable gantry 820, thereby freeing up space and reducing an outer volume of the helical radiation delivery system 800 to provide space for the gimbled head (not shown in FIG. 1A). The patient 830 may be simultaneously moved through the rotatable gantry 820 on a treatment couch 840. In some embodiments (sometimes referred to as, "axial delivery" or "axial radiation treatment delivery"), the helical radiation delivery system 800 may provide rotational delivery of the treatment beam, while the treatment couch 840 is at a fixed position. In some embodiments (sometimes referred to as, "helical delivery" or "helical radiation treatment delivery"), the helical radiation delivery system 800 may provide a helical radiation treatment delivery of the treatment beam from the rotatable gantry 820 by rotating the rotatable gantry 820, while the patient 830 moves through the rotatable gantry 820 on the treatment couch 840. In some embodiments, (sometimes referred to as, "non-rotational delivery" or "non-rotational treatment delivery") the helical radiation delivery system 800 may provide non-rotational delivery of the treatment beam from the rotatable gantry 820 by maintaining the rotatable gantry 820 in a stationary (e.g., a fixed angle) position, while the patient 830 is at a fixed position or while the patient 830 moves through the rotatable gantry 820.

A rotary joint 1000 may be coupled to the rotatable gantry 820 via an RF waveguide 1005 and a conduit 1006. In some embodiments, the rotary joint 1000 may be multifunctional and include a slip ring (not shown in FIG. 1A) to collectively provide alternating current power, air, fluid, control, high speed data signals, and radio frequency (RF) power supply to the rotatable gantry 820 through both the RF waveguide 1005 and the conduit 1006. In some embodiments, the rotary joint 1000 may provide RF power via the RF waveguide 1005 to the rotatable gantry 820 while having a small-diameter slip ring (smaller than the aforementioned slip ring) concentric with rotary joint 1000 to provide alternating current power, air, fluid, control, and data signals to the rotatable gantry 820 via conduit 1006 in a manner that reduces manufacturing cost of the radiation delivery system 100a. In some embodiments, a slip ring (not shown in FIG. 1A) may remain on the rotatable gantry 820 itself to allow the transmission of alternating current power, air, fluid, control, and data signals to the rotatable gantry 820 via conduit 1006, while the rotary joint 1000 provides RF power to the rotatable gantry 820 via the RF waveguide 1005.

In some embodiments, the rotary joint 1000 may be coupled to a partition 1001, while the partition 1001 is positioned between the rotatable gantry 820 and an external system 1002. In some embodiments, a microwave source 1010, a modulator 1020, a radio frequency (RF) isolator 1030, a power distribution unit (PDU) 1040, a fluid temperature control unit (TCU) 1060, a pump 1065, and a processing device 1230 may be separate components. In some embodiments, the microwave source 1010, the modulator 1020, the RF isolator 1030, the PDU 1040, the fluid TCU 1060, the pump 1065, and the processing device 1230 are included in the external system 1002. The rotary joint 1000 may provide a physical connection from the LINAC 850 to external system 1002 that is configured to transport to the rotatable gantry 820 at least one of RF power, electric power (e.g., less than 125 kV), high-voltage electric power (e.g., equal to or greater than 125 kV), a cooling liquid (e.g., water, etc.), air, or high-speed data.

The partition 1001 may be implemented using various configurations (e.g. webbed, opaque, gridded, perforated, solid, etc.) and using any appropriate material (e.g. lead, concrete, brick, wood, metals, metallic alloys, polymers, etc.). In an embodiment, the partition 1001 is capable of providing EMI and magnetic shielding to sensitive components (e.g., the microwave source 1010, the modulator 1020, the RF isolator 1030, the PDU 1040, the fluid TCU 1060, the pump 1065, and the processing device 1230) from electromagnetic radiation and magnetic fields generated by the helical radiation delivery system 800 while in operation. By locating the sensitive components (e.g., one or more components of external system 1002) on an opposite side 1007 of partition 1001 in relation to the rotatable gantry 820, the sensitive components would require reduced EMI or magnetic field shielding on the components themselves to function properly. However, without such component-specific shielding and without a partition 1001, the helical radiation delivery system 800 would be unable to operate properly and treatment, imaging, and measurement capabilities/accuracy would be diminished as a result.

As shown in FIG. 1A, the rotary joint 1000 may be embedded (e.g., structurally implanted with fasteners) into the partition 1001. The rotary joint 1000 may comprise the RF waveguide 1005, the conduit 1006, and slip ring (not shown in FIG. 1A) as described herein. The rotary joint 1000 may be implemented or realized in any appropriate shape (e.g., cylinder, etc.) and/or using any appropriate material (e.g., metals, metallic alloys, polymers, etc.).

In some embodiments, the external system 1002, which is positioned off the rotatable gantry 820 and on the opposite side 1007 of the partition 1001, is a radiation source, such as the microwave source 1010, used to generate electromagnetic waves for the LINAC 850. The electromagnetic waves may be provided to the LINAC 850 via the rotary joint 1000 and through the RF waveguide 1005. In some embodiments, the microwave source 1010 may include one or more of a klystron 1012 or a magnetron 1014. In some embodiments, the external system 1002 may be the modulator 1020 (e.g., a solid state modulator) to adjust the electromagnetic waves for the LINAC 850. The modulator 1020 may be positioned off the rotatable gantry 820 while providing adjusted electromagnetic waves to the LINAC 850 via the rotary joint 1000 and through the RF waveguide 1005. By implementing the klystron 1012 along with the LINAC 850 optimized for 8 megaelectronvolts (MeV) at a target, outputs exceeding 2000 centigray per minute (cGy/min) may be achieved.

In some embodiments, the external system 1002 is the RF isolator 1030 to protect the RF source of the helical radiation delivery system 800 from a signal reflection of a signal. The RF isolator 1030 may be positioned off the rotatable gantry 820 and on the opposite side 1007 of the partition 1001 while transmitting the signal via the rotary joint 1000 and through the RF waveguide 1005. The RF isolator 1030 may be coupled to the microwave source 1010.

In some embodiments, the external system 1002 is the power distribution unit (PDU) 1040 to supply energy to the helical radiation delivery system 800. The energy may be in the form of alternating current power. The PDU 1040 may be positioned off the rotatable gantry 820 and on the opposite side 1007 of the partition 1001 while providing energy to the rotatable gantry 820 via the rotary joint 1000 and through the conduit 1006.

In some embodiments, the external system 1002 is an air distribution unit (ADU) 1050 to supply air to the helical radiation delivery system 800. The ADU 1050 may be positioned off the rotatable gantry 820 and on the opposite side 1007 of the partition 1001, while providing air to the rotatable gantry 820 via the rotary joint 1000 and through the conduit 1006.

In some embodiments, the external system 1002 is a fluid temperature control unit (TCU) 1060 comprising a pump 1065 to provide a fluid (e.g., a water, a coolant, etc.) to the helical radiation delivery system 800 at a determined temperature. The fluid TCU 1060 may be positioned off the rotatable gantry 820 and on the opposite side 1007 of the partition 1001 while providing fluid to the rotatable gantry 820 via the rotary joint 1000 and through the conduit 1006. By doing so, the fluid's temperature may be controlled at the start of receiving the fluid from a public source rather than controlling the fluid's temperature upon the fluid reaching the rotatable gantry 820 of the helical radiation delivery system 800.

In some embodiments, the external system 1002 is the processing device 1230 that may modify a treatment delivery to the patient 830. The processing device 1230 may be positioned off the rotatable gantry 820 and on the opposite side 1007 of the partition 1001 while being coupled to the microwave source 1010, the modulator 1020, the RF isolator 1030, the PDU 1040, the fluid TCU 1060, and the pump 1065. The processing device 1230 may be configured to receive information regarding RF power, energy, air, fluid, control, and high speed data signals from the helical radiation delivery system 800 in operation as well as send information to the helical radiation delivery system 800 through the conduit 1006.

In some embodiments, the helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In some embodiments, the helical radiation delivery system 800 may also include a secondary imaging system consisting of a kV imaging source 810 (e.g., an x-ray tube) mounted orthogonally relative to the LINAC 850 (e.g., separated by 90 degrees) on the rotatable gantry 820 and may be aligned to project an imaging x-ray beam at a target region and to illuminate an imaging plane of a detector after passing through the patient 130. In some embodiments, the helical radiation delivery system 800 may include additional kV imaging sources to improve imaging capabilities as well as provide additional imaging capabilities as further discussed below. In some embodiments, the X-ray tube is configured to receive high voltage electric power (e.g., greater than or equal to 125 kV) via the physical connection and generate an image using the electric power.

In some embodiments, the helical radiation delivery system 800 may include scalable features such as a magnetic resonance imaging (MRI) system (not shown in FIG. 1A) to generate one or more magnetic resonance images of the patient 830. In some embodiments, the helical radiation delivery system 800 may also include a computerized tomography (CT) system (not shown in FIG. 1A) to perform one or more CT scans of the patient 830, a positron emission tomography (PET) system (not shown in FIG. 1A) to perform one or more PET scans of the patient 830, and/or a single-photon emission computerized tomography (SPECT) system (not shown in FIG. 1A) to perform one or more SPECT scans of the patient 830.

Figure 1B:
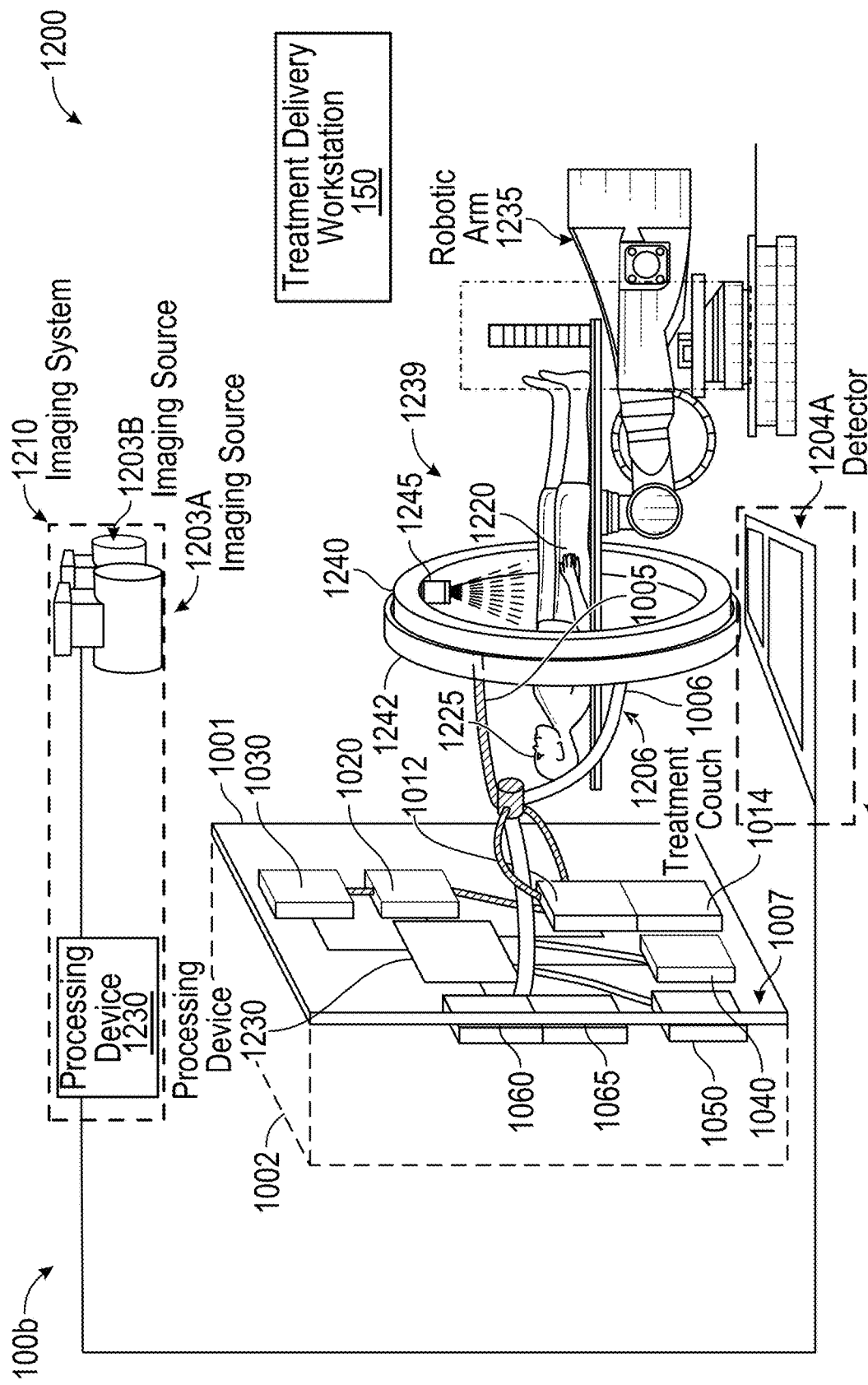
FIG. 1B illustrates a radiation treatment system, in accordance with embodiments described herein.

FIG. 1B illustrates a radiation delivery system 100b, in accordance with embodiments described herein. The radiation delivery system 100b may comprise an image-guided radiation treatment (IGRT) system 1200, a rotary joint 1000, and an external system 1002.

As shown, FIG. 1B illustrates a configuration of an IGRT system 1200. In the illustrated embodiments, the IGRT system 1200 includes a linear accelerator (LINAC) 1201 and an MLC 1205 coupled with the distal end of the LINAC 1201 to shape the treatment beam. In some embodiments, the LINAC 1201 is mounted on the interior of a rotatable gantry 1240 (e.g., a ring) in order to position the LINAC 1201 to irradiate a pathological anatomy (e.g., target) with beams delivered from many angles, in many planes, in an operating volume around a patient. In some embodiments, rotatable gantry 1240 may be rotatable gantry 820 in FIG. 1A. Treatment may involve beam paths with a single isocenter, multiple isocenters, or with a non-isocentric approach.

The IGRT system 1200 may perform the functions described within FIG. 1A. Non-coplanar capability may also be achieved by the rotatable gantry 1240 with the addition of a gimbled head (not shown in FIG. 1B). The rotatable gantry 1240 may be attached to a stationary support ring 1242, which may be coupled to an arm and rail system (not shown in FIG. 1B) that moves the rotatable gantry 1240 and stationary support ring 1242 along one or more axes (e.g., along an axis that extends from a head to a foot of a treatment couch 1206). The treatment couch 1206 may tilt vertically though the use of a robotic arm 1235 to angle a patient 1225 in such a way to further support non-coplanar capabilities of the LINAC 1201.

The LINAC 1201 may be positioned at multiple different nodes (predefined positions at which the LINAC 1201 is stopped and radiation may be delivered) during treatment by rotating the rotatable gantry 1240 up to and in excess of 360 degrees. At the nodes, the LINAC 1201 of IGRT system 1200 can deliver one or more radiation treatment beams to a target, where the radiation beam shape is determined by the leaf positions in the MLC 1205. The nodes may be arranged in an approximately spherical distribution about a patient upon both rotating the rotatable gantry 1240 and pivoting the LINAC 1201 in relation to a stationary support ring 1242. In other words, the LINAC 1201 may be mounted on a gimbled head along with the RF rotary joint 1000, such that when the rotatable gantry 1240 is rotated there would be the capability to independently tilt the LINAC 1201 to provide non-coplanar angles for beam delivery. The particular number of nodes and the number of treatment beams applied at each node may vary as a function of the location and type of pathological anatomy to be treated.

In some embodiments, the rotatable gantry 1240 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

In some embodiments, the radiation delivery system 100*b* may include an external system 1002 that comprises an imaging system 1210 having a processing device 1230 connected with x-ray sources 1203A and 1203B (i.e., imaging sources) and fixed x-ray detectors 1204A and 1204B. The imaging system 1210 may be utilized to generate additional imaging beams. Alternatively, the x-ray sources 1203A, 1203B and/or fixed x-ray detectors 1204A, 1204B may be mobile, in which case they may be repositioned to maintain alignment with the target, or alternatively to image the target from different orientations or to acquire many x-ray images and reconstruct a three-dimensional (3D) cone-beam CT.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on the treatment couch 1206 during treatment) and to illuminate imaging planes of respective fixed x-ray detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In some embodiments, the radiation delivery system 100*b* also includes a secondary imaging system 1239. Secondary imaging system 1239 may be a Cone Beam Computed Tomography (CBCT) imaging system. Alternatively, other types of imaging systems may be used as described with FIG. 1A. In some embodiments, imaging system 1239 may also perform the functions described with FIG. 1A with the implementation of the rotary joint 1000, the partition 1001, and the external system 1002. The secondary imaging system 1239 includes the rotatable gantry 1240 attached to the stationary support ring 1242, which is coupled to an arm and rail system (not shown in FIG. 1B) that moves the rotatable gantry 1240 along one or more axes (e.g., along an axis that extends from a head to a foot of the treatment couch 1206). An imaging source (not shown in FIG. 1B) and a detector (not shown in FIG. 1B) may be mounted to the rotatable gantry 1240. The rotatable gantry 1240 may rotate more than 360 degrees about the axis that extends from the head to the foot of the treatment couch 1206. In doing so, the rotatable gantry 1240 may provide a continuous rotation that may travel multiple rotations in excess of 360 degrees. Accordingly, the imaging source and detector may be positioned at numerous different angles. In some embodiments, the imaging source is an x-ray source and the detector is an x-ray detector and either may be mounted to the rotatable gantry 1240 or the stationary support ring 1242.

As shown in FIG. 1B, the image-guided radiation treatment system 1200 may further be associated with a treatment delivery workstation 150. The treatment delivery workstation may be remotely located from the IGRT system 1200 in a different room than the treatment room in which the IGRT system 1200 and patient are located (e.g. on the opposite side 1007 of partition 1001). The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
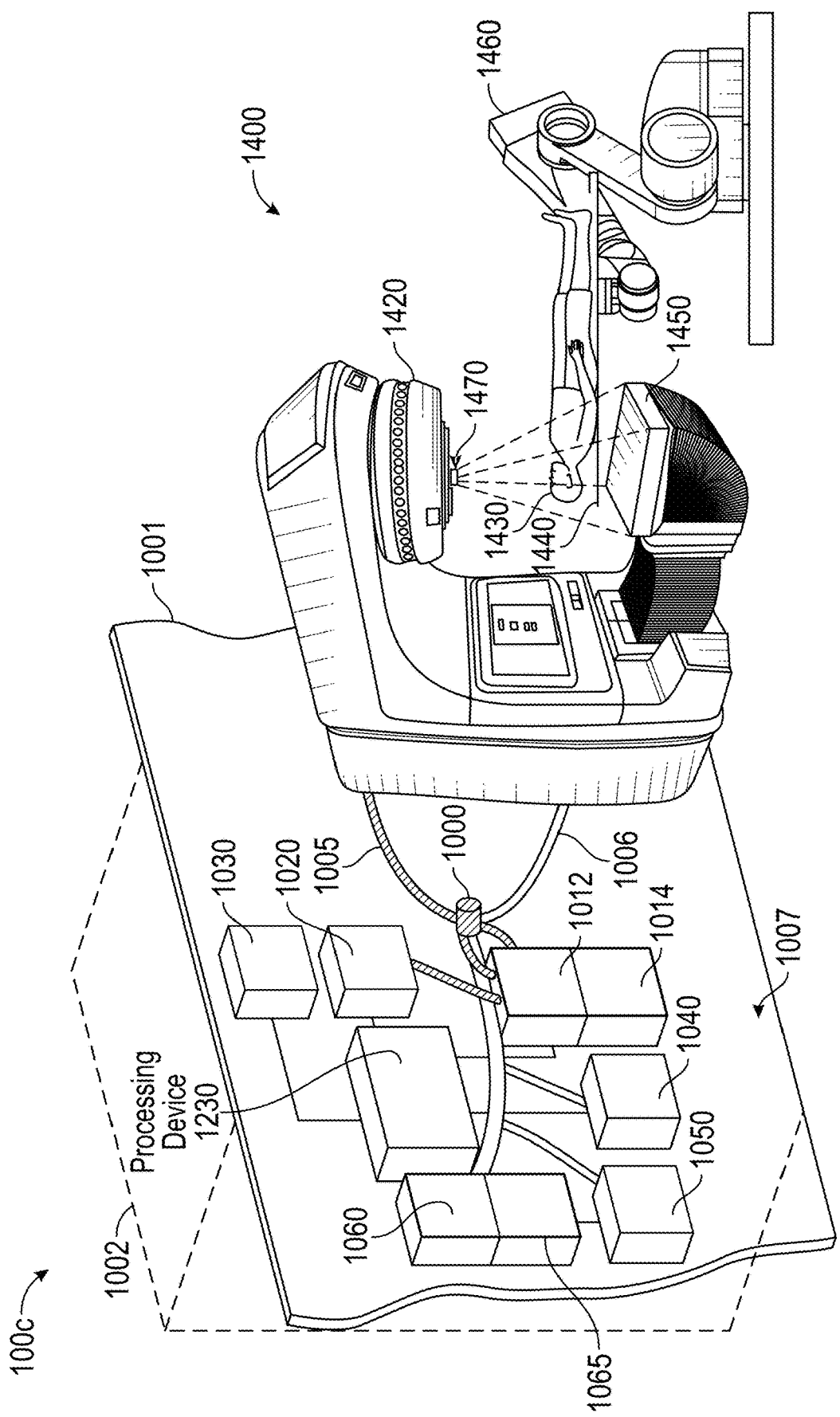
FIG. 1C illustrates a radiation treatment system, in accordance with embodiments described herein.

FIG. 1C illustrates a radiation delivery system 100*c*, in accordance with embodiments described herein. The radiation delivery system 100*c* may comprise a C-arm gantry-based radiation treatment system 1400, a rotary joint 1000, and an external system 1002.

In some embodiments, in the C-arm gantry-based radiation treatment system 1400 the beam energy of a LINAC may be adjusted during treatment and may allow the LINAC to be used for both x-ray imaging and radiation treatment. In some embodiments, the C-arm gantry-based radiation treatment system 1400 may include an onboard kV imaging system to generate x-ray images and a separate LINAC to generate the higher energy therapeutic radiation beams. The C-arm gantry-based radiation treatment system 1400 includes a C-arm gantry 1410, a LINAC 1420, an MLC 1470 coupled with the distal end of the LINAC 1420 to shape the beam, and a portal imaging detector 1450. The C-arm gantry 1410 may be rotated to an angle corresponding to a selected projection and used to acquire an x-ray image of a VOI of a patient 1430 on a treatment couch 1440. The external system 1002 may be provided off the gantry as discussed with respect to FIG. 1A and shown in FIG. 1C. In some embodiments, the external system 1002 may be provided off the gantry above the C-arm gantry 1410 by having the rotary joint 1000 embedded (e.g., structurally implanted with fasteners) into a ceiling (not shown in FIG. 1C) of a treatment room. In some embodiments, the rotary joint 1000 may be embedded into the C-arm gantry 1410 itself.

In some embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 1D:
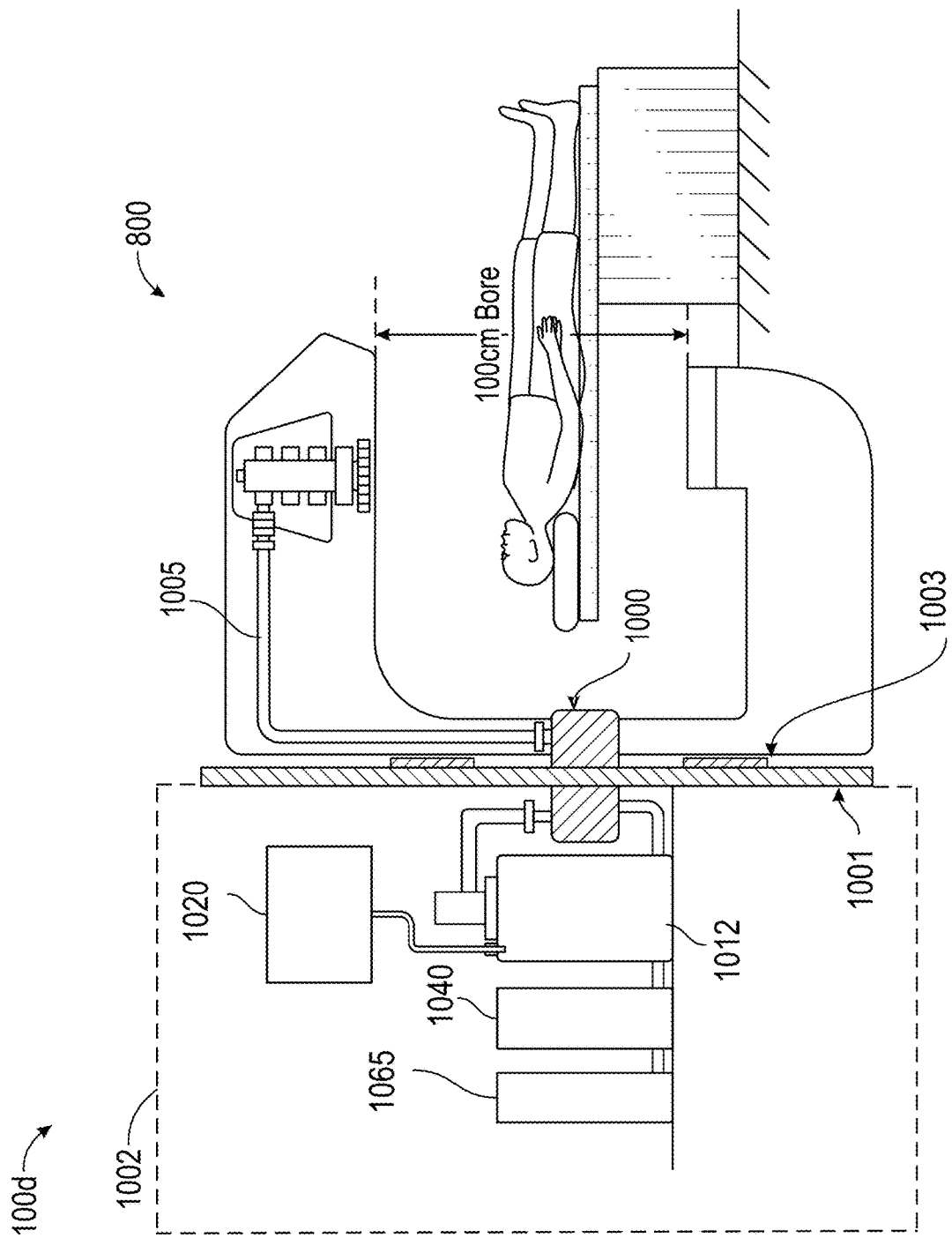
FIG. 1D illustrates a radiation treatment system, in accordance with embodiments described herein.

FIG. 1D illustrates a radiation delivery system 100d, in accordance with embodiments described herein. Similar to FIG. 1A, the radiation delivery system 100d may include the helical radiation delivery system 800, the rotary joint 1000, the RF waveguide 1005, the partition 1001, and the external system 1002; each configured to operate as discussed with respect to FIG. 1A. The external system 1002 may include the modulator 1020, the klystron 1012, the power distribution unit (PDU) 1040, and/or the pump 1065.

The radiation delivery system 100d includes a small-diameter slip ring 1003 concentric (coaxially around) with rotary joint 1000 that reduces cost and further simplifies the gantry of the radiation delivery system 100d. In some embodiments, the diameter of the small-diameter slip ring 1003 is smaller than the diameter of the rotary joint 1000. In some embodiments, the small-diameter slip ring is configured to provide alternating current power and/or data signals to the helical radiation delivery system 800, while the rotary joint 1000 is configured to provide RF power, air, and/or cooling fluid (e.g., water) to the helical radiation delivery system 800.

Some patients may be prone to experiencing claustrophobia when undergoing medical imaging procedures. To reduce claustrophobia, the radiation delivery system 100d may include a bore opening that has a diameter of up to 100 centimeters (cm).

Figure 2:
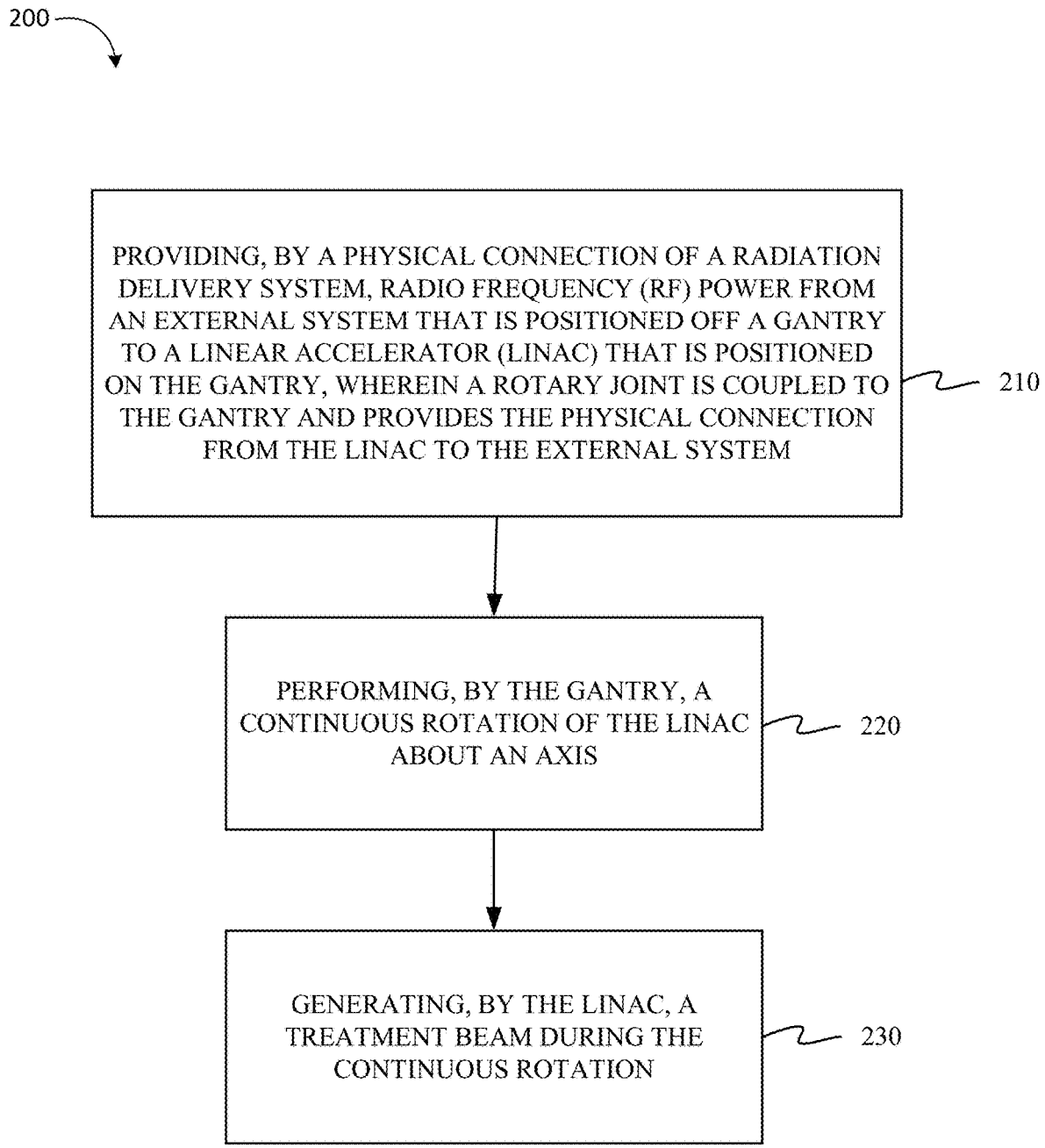
FIG. 2 depicts a flow diagram of a method of utilizing a continuously rotating gantry and a rotary joint to transmit data and generate a treatment beam, in accordance with embodiments of the disclosure.

FIG. 2 depicts a flow diagram of a method 200 of utilizing a continuously rotating gantry and a rotary joint to transmit data and generate a treatment beam, in accordance with embodiments of the disclosure. Method 200 may be performed, at least in part, by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, various portions of method 200 may be performed by the helical radiation delivery system 800 in FIG. 1A. In some embodiments, various portions of method 200 may be performed by the IGRT system 1200 in FIG. 1B. In some embodiments, various portions of method 200 may be performed by the C-arm radiation delivery system 1400 in FIG. 1C.

With reference to FIG. 2, method 200 illustrates example functions used by various embodiments. Although specific function blocks ("blocks") are disclosed in method 200, such blocks are examples. That is, embodiments are well suited to performing various other blocks or variations of the blocks recited in method 200. It is appreciated that the blocks in method 200 may be performed in an order different than presented, and that not all of the blocks in method 200 may be performed.

Method 200 begins at block 210, where radio frequency (RF) power from an external system that is positioned off a gantry is provided (e.g., transmitted, delivered), by a physical connection, to a linear accelerator (LINAC) that is positioned on the gantry. In some embodiments, the physical connection is configured to transport to the rotatable gantry 820 at least one of RF power, electric power (e.g., less than 125 kV), high-voltage electric power (e.g., equal to or greater than 125 kV), a cooling liquid (e.g., water, etc.), air, or high-speed data. The physical connection is provided from the LINAC to the external system by a rotary joint that is coupled to both the gantry and external system. In some embodiments, the rotary joint may be coupled to a partition that does not inhibit a physical connection between the LINAC and external system.

At block 220, the gantry performs a continuous rotation of the LINAC about an axis. In some embodiments, the gantry may perform a continuous rotation that may travel multiple rotations in excess of 360 degrees.

At block 230, an accelerating structure generates a treatment beam during a continuous rotation of the gantry. In some embodiments, multiple treatment beams having different energy levels may be used.

Figure 3:
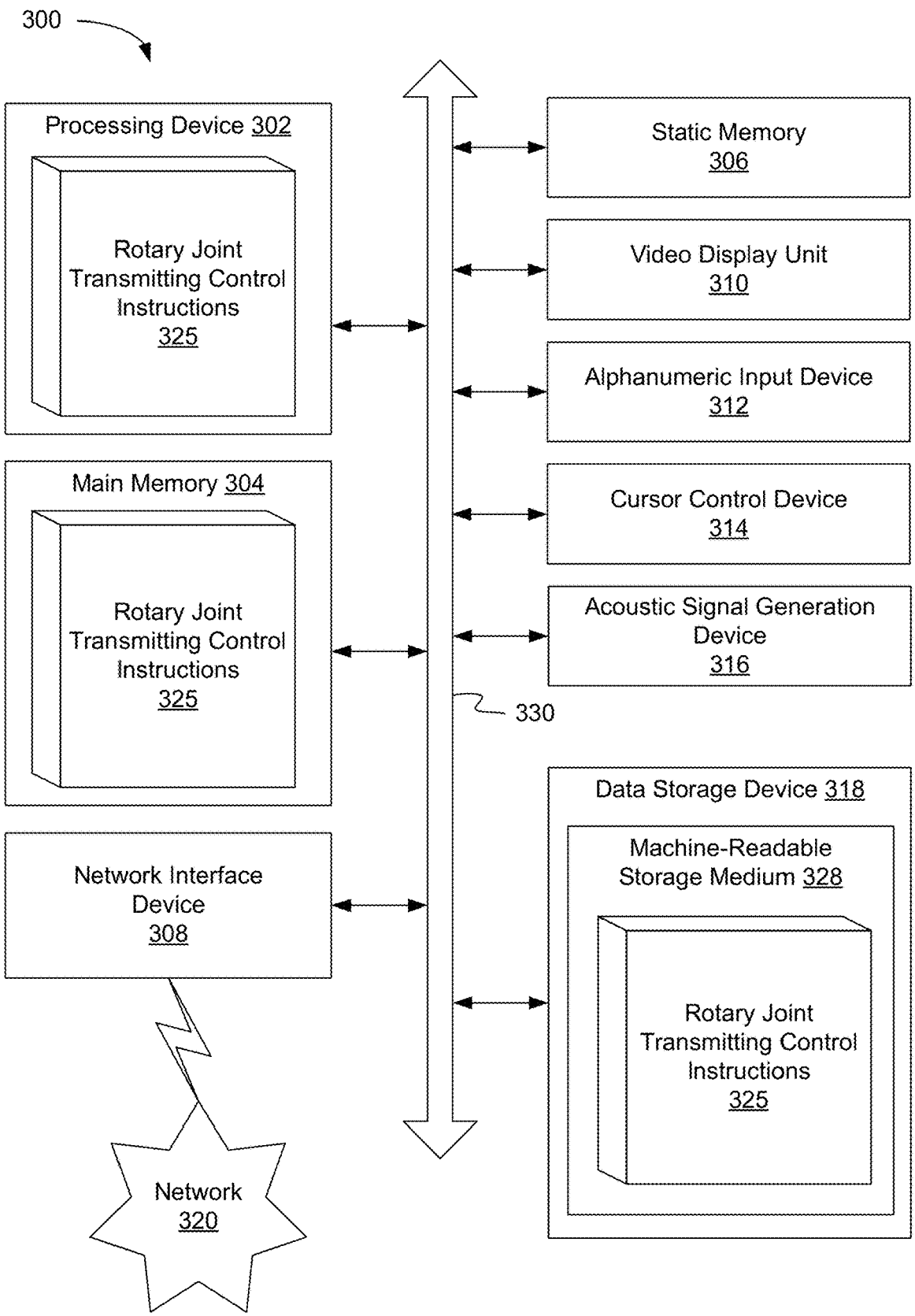
FIG. 3 is a block diagram of an example computing device that may perform one or more of the operations described herein, in accordance with some embodiments.

FIG. 3 is a block diagram of an example computing device 300 that may perform one or more of the operations described herein, in accordance with some embodiments. Computing device 300 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 300 may include a processing device (e.g., a general purpose processor, a PLD, etc.) 302, a main memory 304 (e.g., synchronous dynamic random access memory (DRAM), read-only memory (ROM)), a static memory 306 (e.g., flash memory and a data storage device 318), which may communicate with each other via a bus 330.

Processing device 302 may be provided by one or more general-purpose processing devices such as a microprocessor, central processing unit, or the like. In an illustrative example, processing device 302 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 302 may also comprise one or more special-purpose processing devices such as an application specific integrated circuit (ASIC), a field programmable gate array (FPGA), a digital signal processor (DSP), network processor, or the like. The processing device 302 may be configured to execute the operations described herein, in accordance with one or more aspects of the present disclosure, for performing the operations and steps discussed herein.

Computing device 300 may further include a network interface device 308 which may communicate with a network 320. The computing device 300 also may include a video display unit 310 (e.g., a liquid crystal display (LCD) or a cathode ray tube (CRT)), an alphanumeric input device 312 (e.g., a keyboard), a cursor control device 314 (e.g., a mouse) and an acoustic signal generation device 316 (e.g., a speaker). In one embodiment, video display unit 310, alphanumeric input device 312, and cursor control device 314 may be combined into a single component or device (e.g., an LCD touch screen).

Data storage device 318 may include a computer-readable storage medium 328 on which may be stored one or more sets of instructions that may include rotary joint transmitting control instructions 325 for carrying out the operations described herein, in accordance with one or more aspects of the present disclosure. The instructions may also reside, completely or at least partially, within main memory 304 and/or within processing device 302 (e.g., processing device 1230 in FIG. 1) during execution thereof by computing device 300, main memory 304 and processing device 302 also constituting computer-readable media. The instructions may further be transmitted or received over a network 320 via network interface device 308.

While computer-readable storage medium 328 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.).

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Reference throughout this specification to "one embodiment" or "an embodiment" means that a particular feature, structure, or characteristic described in connection with the embodiments included in at least one embodiment. Thus, the appearances of the phrase "in one embodiment" or "in an embodiment" in various places throughout this specification are not necessarily all referring to the same embodiment.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the present disclosure, including what is described in the Abstract, is not intended to be exhaustive or to limit implementations of the present disclosure to the precise forms disclosed. While specific implementations of, and examples for, the present disclosure are described herein for illustrative purposes, various equivalent modifications are possible within the scope of the present disclosure, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. A radiation delivery system, comprising:
a gantry to extend along one or more axes, wherein the gantry is to provide a continuous rotation;
a linear accelerator (LINAC) coupled to the gantry, wherein the LINAC is to generate a treatment beam;
an external system, comprising a processor, that is positioned off the gantry; and
a rotary joint coupled to the gantry, wherein the rotary joint provides a physical connection from the LINAC to the external system, wherein the physical connection is to transport one or more of data or electric power.

2. The radiation delivery system of claim 1, wherein the gantry comprises a ring gantry or a C-arm gantry.

3. The radiation delivery system of claim 1, wherein the continuous rotation is to travel multiple rotations.

4. The radiation delivery system of claim 1, wherein the external system provides electromagnetic waves to the LINAC via the rotary joint.

5. The radiation delivery system of claim 4, wherein the external system comprises a klystron.

6. The radiation delivery system of claim 5, wherein the external system to adjust high-voltage pulses that drive the klystron to produce adjusted electromagnetic waves for the LINAC and provide the adjusted electromagnetic waves to the LINAC via the rotary joint.

7. The radiation delivery system of claim 4, wherein the external system comprises a magnetron.

8. The radiation delivery system of claim 7, wherein the external system to adjust high-voltage pulses that drive the magnetron to produce adjusted electromagnetic waves for the LINAC and provide the adjusted electromagnetic waves to the LINAC via the rotary joint.

9. The radiation delivery system of claim 1, wherein the external system to protect components from a signal reflection of a signal that is transmitted via the rotary joint.

10. The radiation delivery system of claim 1, wherein the external system to provide a fluid at a determined temperature to the gantry via the rotary joint.

11. The radiation delivery system of claim 1, wherein the external system to supply energy to the gantry via the rotary joint.

12. The radiation delivery system of claim 1, wherein the external system to create timing instructions for the LINAC and provide the timing instructions to the LINAC via the rotary joint.

13. The radiation delivery system of claim 1, wherein the external system to supply air to the gantry via the rotary joint.

14. The radiation delivery system of claim 1, further comprising:
a physical barrier between the external system and the gantry, wherein the physical barrier is opaque, perforated, or webbed.

15. The radiation delivery system of claim 1, further comprising:
a computerized tomography (CT) system to perform one or more CT scans.

16. The radiation delivery system of claim 1, further comprising:
an imaging panel; and
an X-ray tube positioned on the gantry, wherein the X-ray tube is to receive the electric power via the physical connection, generate X-rays, and record an image using the imaging panel.

17. A method, comprising:
providing, by a physical connection of a radiation delivery system, one or more of data or electric power from an external system, comprising a processor, that is positioned off a gantry to a linear accelerator (LINAC) that is positioned on the gantry, wherein a rotary joint is coupled to the gantry, and wherein the rotary joint provides the physical connection from the LINAC to the external system;
performing, by the gantry, a continuous rotation of the LINAC about an axis; and
generating, by the LINAC, a treatment beam during the continuous rotation.

18. The method of claim 17, wherein the gantry comprises a ring gantry or a C-arm gantry.

19. The method of claim 17, wherein the radiation delivery system delivers a non-coplanar treatment beam by pivoting the LINAC out of a plane of rotation of the gantry.

20. The method of claim 17, wherein the continuous rotation is to travel multiple rotations.

* * * * *